United States Patent
Pan et al.

(10) Patent No.: US 10,900,818 B2
(45) Date of Patent: Jan. 26, 2021

(54) APPARATUS AND METHODS FOR DIGITAL DROPLET FLOWMETRY

(71) Applicant: THE REGENTS OF THE UNIVERSITY OF CALIFORNIA, Oakland, CA (US)

(72) Inventors: Tingrui Pan, Woodland, CA (US); Yahui Yang, Davis, CA (US); Zecong Fang, Davis, CA (US); Siyuan Xing, Davis, CA (US); Ruya Li, Davis, CA (US); Hong Liu, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/538,307

(22) Filed: Aug. 12, 2019

(65) Prior Publication Data
US 2020/0041319 A1 Feb. 6, 2020

Related U.S. Application Data

(63) Continuation of application No. PCT/US2018/018065, filed on Feb. 13, 2018.
(Continued)

(51) Int. Cl.
*G01F 1/64* (2006.01)
*A61B 5/145* (2006.01)
*A61B 5/00* (2006.01)

(52) U.S. Cl.
CPC ............ *G01F 1/64* (2013.01); *A61B 5/14517* (2013.01); *A61B 5/4266* (2013.01); *A61B 5/6804* (2013.01)

(58) Field of Classification Search
None
See application file for complete search history.

(56) References Cited

U.S. PATENT DOCUMENTS 6,321,791 B1    11/2001   Chow
7,458,661 B2 *   12/2008   Kim ........................ B41J 2/005
                                                  347/45
(Continued)

FOREIGN PATENT DOCUMENTS

WO      2018148756 A1    8/2018

OTHER PUBLICATIONS

ISA,KR, Korean Intellectual Property Office (KIPO), International Search Report and Written Opinion dated Jun. 25, 2018, related PCT international application No. PCT/US2018/018065, pp. 1-10, claims searched, pp. 11-14.
(Continued)

*Primary Examiner* — Harshad R Patel
(74) *Attorney, Agent, or Firm* — Kurt T. Mulville; VLP Law Group, LLLP

(57) ABSTRACT

A fabric based digital droplet flowmetry (DDF) method and platform are provided utilizing a fluid collection network, a microfluidic junction for droplet formation and removal, and digital counting and measurement circuitry. The fluidic junction has a droplet emitter, such as a nozzle, and droplet receiver separated by a gap. The measurement circuitry detects the transient formation of a liquid bridge (the closed-circuit state) and the breakup of the bridge (the open-circuit state) as an electrical switching event. The duration of the bridge formation only lasts for a few milliseconds. The platform produces consistent droplet volume over varying flow rates and droplet size is controlled by the selection of structural parameters such as nozzle dimensions, channel geometries, surface wettability, and inlet/outlet pressures.

20 Claims, 7 Drawing Sheets

Related U.S. Application Data

(60) Provisional application No. 62/458,094, filed on Feb. 13, 2017.

(56) References Cited

U.S. PATENT DOCUMENTS

2011/0072909 A1   3/2011  Wenger
2011/0209998 A1   9/2011  Shenderov

OTHER PUBLICATIONS

Moiseeva, E.V. et al., "Thin-film electrode based droplet detection for microfluidic systems", Sensors and Actuators B 155 (2011) 408-414, published onlilne Nov. 24, 2010.
Teh, Shia-Yen et al., "Droplet microfluidics", Lab Chip, 2008, 8, 198-220, published online Jan. 11, 2008.

* cited by examiner

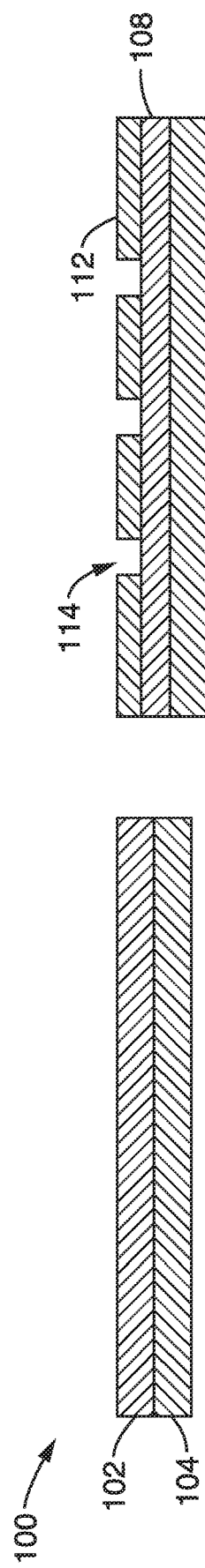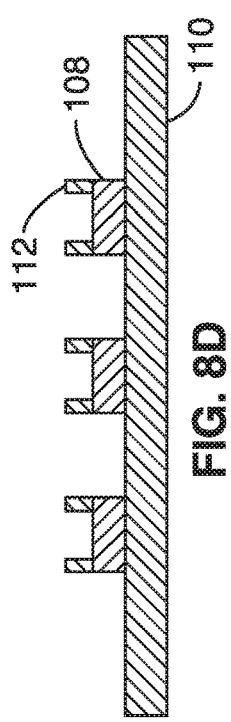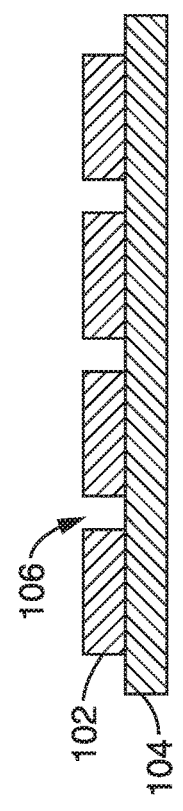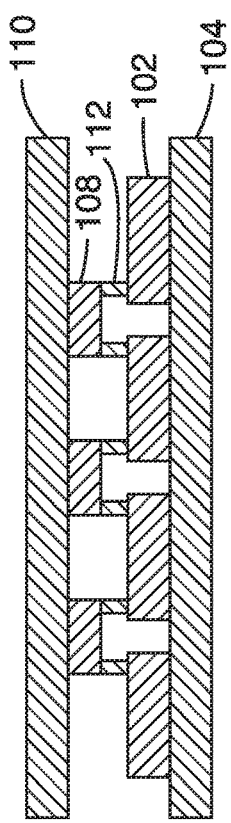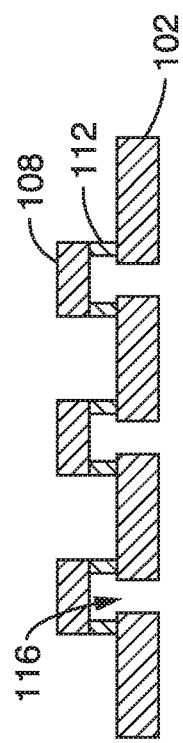

APPARATUS AND METHODS FOR DIGITAL DROPLET FLOWMETRY

CROSS-REFERENCE TO RELATED APPLICATIONS

This application claims priority to, and is a 35 U.S.C. § 111(a) continuation of, PCT international application number PCT/US2018/018065 filed on Feb. 13, 2018, incorporated herein by reference in its entirety, which claims priority to, and the benefit of, U.S. provisional patent application Ser. No. 62/458,094 filed on Feb. 13, 2017, incorporated herein by reference in its entirety. Priority is claimed to each of the foregoing applications.

STATEMENT REGARDING FEDERALLY SPONSORED RESEARCH OR DEVELOPMENT

This invention was made with Government support under DBI1256193, awarded by the National Science Foundation, and under 1R21CA173243-01A1, awarded by the National Institutes of Health. The Government has certain rights in the invention.

The above-referenced PCT international application was published as PCT International Publication No. WO 2018/148756 on Aug. 16, 2018, which publication is incorporated herein by reference in its entirety.

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

INCORPORATION-BY-REFERENCE OF COMPUTER PROGRAM APPENDIX

Not Applicable

BACKGROUND

1. Technical Field

The technology of this disclosure pertains generally to fluid flowmetry systems, and more particularly to devices and methods for microfluidic digital droplet flowmetry and fabric-based digital droplet flowmetry platform suited for analysis of perspiration and other biofluids.

2. Background Discussion

Monitoring the physiological status of the body is essential to an accurate medical assessment of patient health status and to evaluate any potential risks of body malfunctions. Recent advancements in the analyses of biofluids hold the promise of real time and continuous monitoring of physiological and/or pathological states of the human body. Perspiration, for example, has been shown to contain certain metabolic information of the body that can be accessed non-invasively. Perspiration rates, ion concentrations, and pH values of sweat could offer valuable information regarding the hydration level and electrolyte balance inside of the body.

One approach has been to developed sensors integrated onto soft substrates to assess the contents of perspiration. For instance, a MEMS humidity sensor was designed to measure a humidity gradient along the skin surface as an indicator of perspiration level. Biochemical sensors have also been attempted to monitor sweat chemistry such as electrolyte concentrations. Another approach was the creation of a tattoo-like sensing device with printed microelectrodes that was capable of quantifying lactate concentrations in perspiration, which was believed to be closely associated with anaerobic exercise levels of the body.

More importantly, measurement of perspiration rates can closely and precisely track body dehydration levels during physically demanding activities of various occupational groups, such as athletes during intense exercising, soldiers carrying out combat missions, and workers exposed to extreme conditions.

One attempt to measure perspiration rate was with the use of a wearable device, where the perspiration rate was assessed by absorbing the sweat into a porous structure over a defined body surface area. However, these devices would stop performing once the porous structure was fully saturated. Likewise, most known systems require an external collection mechanism or they cannot be continuously employed due to saturation limits. Furthermore, the area of sample collection and evaporation in these systems is not well controlled, leading to potential errors in perspiration measurements and analyses.

Interfacial microfluidics, utilizing a unique gas-liquid-solid interface to confine and propel microflow, has been actively researched because of its simple implementation, self-driven mechanism, and immunity to air cavitation and blockage. Unconventional fibrous materials such as textiles, fibers and papers, have been exploited as wicking substrates in interfacial microfluidic applications, allowing "lab-on-a-paper", "lab-on-a-yarn" and "lab-on-a-film" systems to be developed. These flexible-substrate systems inherit the advantages of interfacial microfluidics, featuring low-cost materials, sustainability and facile fabrication processes which can be quickly scaled up.

For example, widely established testing strips (e.g. pH measurement and pregnancy testing), employ the wicking force generated by capillary absorption of microscopic fibrous/porous structures within the substrate. Similarly, the concept of lab-on-a-paper has enabled versatile point-of-care diagnostic functions using micropatterned multilayer paper substrates. Further integration with conductive ink printing has facilitated quantitative electrochemical analyses on the paper-based devices to assess the concentrations of metallic ions and biomolecules.

Moreover, the textile-based materials, including yarns and fabrics, have generated considerable interest to serve as transport substrates for interfacial microfluidics. Textile-based microfluidics utilize the same wicking principle on a hydrophilic fabric (e.g., cotton yarns) to control the fluidic motion of multiple reagents. Such materials have the potential to be scalable and may be produced by well-established industrial scale manufacturing techniques, such as weaving, knitting, and embroidery reducing overall costs. Various microfluidic operations such as mixing and separation, have also been demonstrated on knitted fabric networks.

Contemporary microfluidic flowmetry can be classified by having thermal or non-thermal flow sensors, based on their principle of operation. Among them, the calorimetric flowmeters are reported to have the highest sensitivity in measurements of small flow rates (i.e., 100 nL/h or 1.6 nL/min), which typically includes one heating element and two temperature sensors located both upstream and downstream of the heating element. The temperature sensors monitor the asymmetry of temperature profile and the shift of maximum temperature in the flow stream. However, one major drawback of these thermal flowmeters is that they are non-linear in nature over their temperature range, and therefore need to be fully calibrated and compensated. In addition, these devices may be subject to fluidic contamination and complexed flow. The undesirable heating process can also be problematic for heat-sensitive fluids, particularly most biological fluids.

More importantly, these types of sensors are still not sensitive enough for extremely low flow measurement. For instance, the measurement errors of the commercial thermal flow sensors are typically capped at about 7.5 nL/min, when the flow rate is below 75 nL/min.

On the other hand, non-thermal flow sensors have also been investigated for low flow rate measurement, including mechanical, acoustic, optical, electromagnetic, differential pressure and Coriolis based flow sensors. However, most non-thermal sensors are not yet competitive with thermal flowmeters for technical and commercial reasons.

In spite of the development of absorptive fibers, papers and sensors, the ability to accurately monitor the perspiration rate in situ and in a real-time fashion without interruption remains challenging. Accordingly, there is a need for surface tension driven microfluidic network on microstructured textile substrates with high wettability contrast that can provide a continuous and unsaturated directional transportation scheme of biofluids on a fabric platform, without the need of any external driven mechanism (e.g., pumps) that can accurately determine flow rates etc.

BRIEF SUMMARY

This present technology describes a wearable microfluidic platform made with conventional fabric materials and laser micromachining providing a digital microfluidic flowmeter to measure the flow rate on patterned fabric surface, called digital droplet flowmetry (DDF). A theoretical model is presented for the wearable interfacial microfluidic platform with various design parameters that have been and optimized for various conditions. In one embodiment, the wearable DDF platform is capable of continuously collecting and measuring perspiration over a defined area of skin surface with high precision (96% on average) in real-time.

The digital microfluidic flowmeter platform can measure ultralow flow rates in a highly digitalized and accurate fashion, utilizing interfacial instability to controllably discretize a continuous flow into minute droplets. The measurement approach based on the interfacial bursting events can be simplified and implemented through a wired or wireless circuit, and the corresponding flow rates can be computed from the droplet volume and the bursting frequency.

The preferred digital droplet flowmetry (DDF) platform generally comprises three main components: a fluid collection network, a microfluidic junction for droplet formation and removal, and digital counting and measurement circuitry. The platform may have 2D and 3D digital droplet microflowmetry device designs that produce consistent droplet volumes. The accuracy and precision of the droplet flowmetry devices are governed by the consistency of the droplet volume over varying flow rates and the resolution of the system can be determined by the smallest droplet size. The produced droplet size is influenced by structural parameters such as nozzle dimensions, channel geometries, surface wettability, and inlet/outlet pressure.

For example, one implementation of a droplet microflowmetry device is structured to permit fluid flow in a cylindrical conduit with a pluggable tubular connection (3D version), and another implementation has a planar configuration that can be readily integrated with standard microfluidic chips or a fabric-based platform (2D version).

In one embodiment, the platform has a digital droplet microflowmeter with a droplet nozzle with a superhydrophobic outer surface, one or more fluid channels and at least one orifice in the nozzle outer surface and a first electrode connected to the droplet nozzle. Opposite the droplet nozzle is a droplet receiver that has a hydrophilic outer surface and a second electrode coupled to the droplet receiver. When a droplet emerges from the droplet nozzle, a transient fluid bridge is formed between the droplet nozzle and the droplet receiver closing the circuit between the first and second electrodes.

In another preferred embodiment, a two-dimensional microflowmeter apparatus is provided that has a hydrophilic fluid flow structure with a first conductor disposed on a hydrophobic porous base material such as a fabric. A second hydrophilic fluid flow structure with a second conductor is positioned adjacent to the first hydrophilic fluid flow structure with the two structures separated by a gap. A controller is coupled to the first and second conductors that is configured to sense a change in impedance between the two conductors. A change in impedance is detected by the controller from the formation of a transient fluid bridge between the first and second hydrophilic fluid flow structures.

The platform uses an interfacial microfluidic scheme to produce consistent droplets that is independent with the flow rate and the gravitational influences. The simple droplet ejecting system can be easily configured with a low-cost measurement circuitry and an optional wireless communication module for automated and accurate in-line assessment of ultralow flow rates in a variety of medical and research settings, such as pediatric drug delivery and physiological flow measurement.

The platform with digital microfluidic flowmeters offers several unique advantages over existing flow sensing technologies: a) a straightforward measurement is derived from a gravity drip method, which calculates the flow rates based on the droplet volume and interfacial rupturing frequency; b) simple device architectures can be implemented with both 2D and 3D versions of the DDF device that can be fabricated in a limited number of steps providing low-cost manufacturing; c) measurement of extremely low flow rates are possible because of the small droplet sizes, as small as 1 pL, that can be produced by the platform; d) scalable measurement ranges from single digit of pL/min to sub-µL/min (spanning over at least five orders of magnitude) can be achieved by altering liquid surface tension, introducing additive energy to the interface, changing surface wettability and interfacial geometries; e) highly adaptive designs of DDF permit various fluidic configurations, e.g., pluggable connection or in-line embedment to tubes or reversible integration with planar microfluidic chips; f) a simple acquisition circuitry basically detects the interfacial rupturing events by measuring AC conductance of the fluid, during which dramatic changes in electrical impedance are triggered; g) extremely low power consumption can be managed using simple circuitry, which can also be turned into a completely passive and wireless circuit for special applications; and h) small dimensions and footprints permit high portability and ease of system integration of the DDF sensors.

The digitalized measurement DDF platform provides fast responses, digital readouts, system flexibility, and continuous performance with flow measurement. Moreover, the DDF platform can be conveniently implemented on a regular apparel or a wearable device, and has the potential of being applied to the dynamic removal, collection and monitoring of biofluids for various physiological and clinical processes.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only:

FIG. 8A to FIG. 8F is a schematic illustration of fabrication steps of a wearable digital droplet flowmeter apparatus according to one embodiment of the technology depicting the steps: FIG. 8A a fabric treated with superhydrophobic coating; FIG. 8B through-holes laser-machined in the fabric; FIG. 8C double-sided tape laser-machined and bonded to a non-woven hydrophilic surface; FIG. 8D microfluidic collection patterns laser-machined from the tape and fabric layers; FIG. 8E alignment and bonding of the top hydrophilic patterns to the bottom superhydrophobic fabric and FIG. 8F release of the solid support.

DETAILED DESCRIPTION

Referring more specifically to the drawings, for illustrative purposes, embodiments of an apparatus and methods for digital droplet microflowmetry and fabrication are generally shown. Embodiments of the technology are described generally in FIG. 1 through FIG. 8F to illustrate the characteristics and functionality of the methods, apparatus and system. It will be appreciated that the methods may vary as to the specific steps and sequence and the systems and apparatus may vary as to structural details without departing from the basic concepts as disclosed herein. The method steps are merely exemplary of the order that these steps may occur. The steps may occur in any order that is desired, such that it still performs the goals of the claimed technology.

Figure 1A:
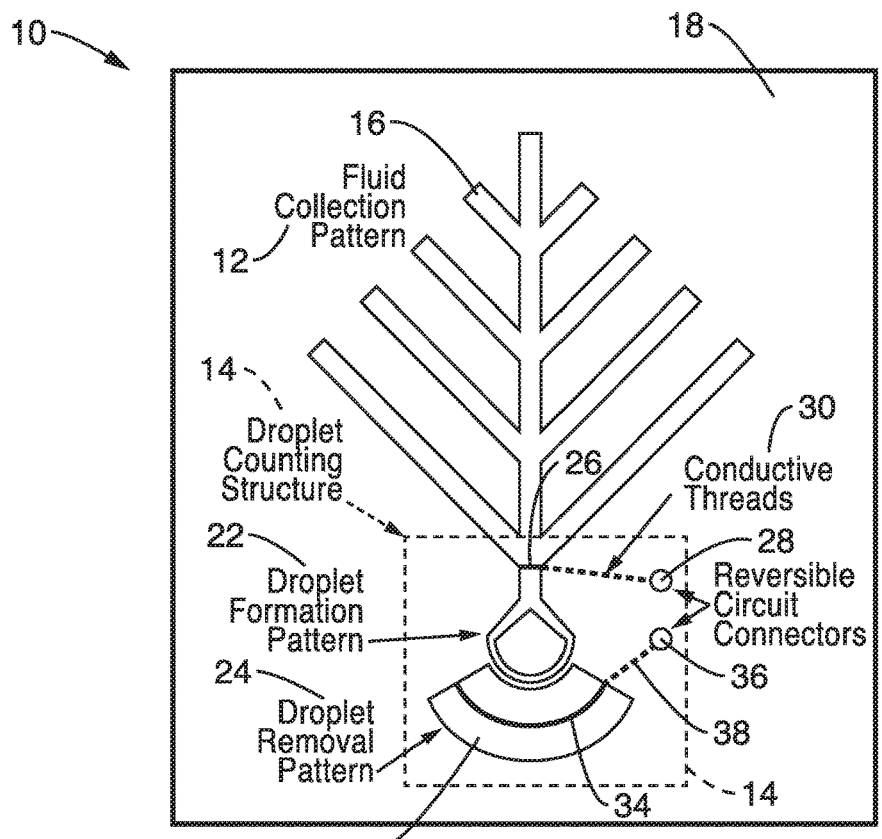
FIG. 1A is a schematic front view illustration of a wearable digital droplet flowmeter according to one embodiment of the technology.
Figure 1B:
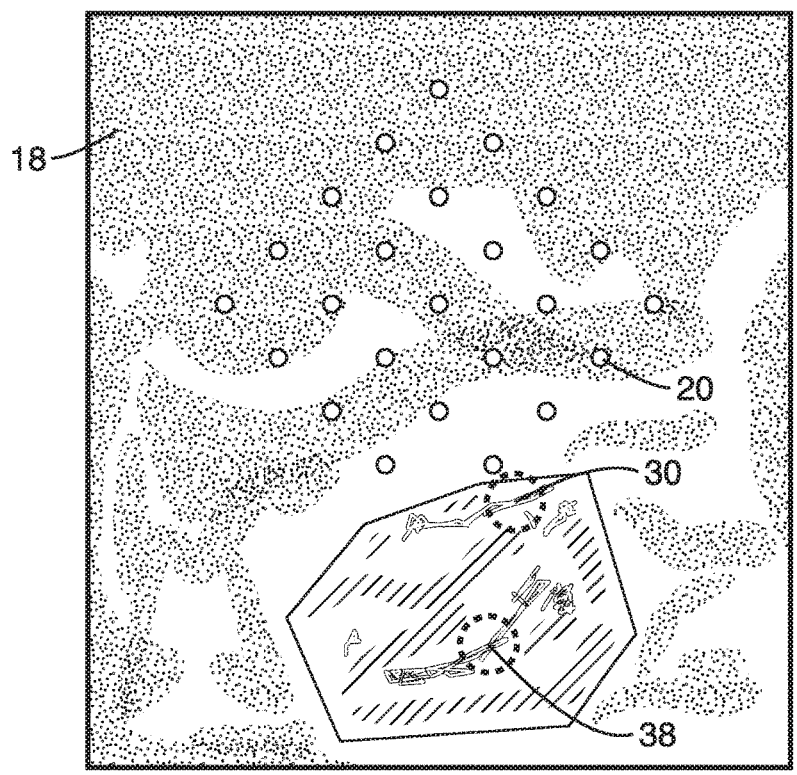
FIG. 1B is a schematic back view illustration of a wearable digital droplet flowmeter showing fluid collection ports according to one embodiment of the technology.

Turning now to FIG. 1A and FIG. 1B, one embodiment of an apparatus for digital droplet miocroflowmetry (DDF) implemented on a textile substrate for real-time flow rate measurements is shown schematically. The microflowmeter platform 10 generally comprises three main components: 1) a fluid collection network 12; 2) a droplet counting structure 14 with a microfluidic junction for droplet formation and removal, and 3) digital counting/measurement circuitry using resistive measurement principles coupled to the droplet counting structure 14.

The collection network 12 of the textile-based fluid transport platform 10 has a pattern of hydrophilic fluid collection material that may include channels mounted to a base substrate 18 of hydrophobic or superhydrophobic material. As used herein, the surface is hydrophobic when its static water contact angle θ is >90° and is hydrophilic when θ is <90° and superhydrophobic when the contact angles of a water droplet exceed 150°.

In the fluid collection design, a through hole structure on the fabric allows the fluid to channel through the fabric and transport onto the hydrophilic fluidic patterns 12 on the external surface of the fabric 18. As a result, the flow of fluid moves towards and accumulates at the bottom of the collection pattern due to gravity. As shown in FIG. 1B, the fluid collection pattern 12 may be open to the bottom side of the base 18 through collection ports 20 to allow fluid collection through the base. Although ports 20 are used to illustrate, other structures such as channels or hydrophilic material can be used to collect and transport fluids.

The fluid collection pattern 12 of FIG. 1A preferably has a number of collection arms 16 that radiate from a central member so that the collected fluid is consolidated at a single point. Although a radiating arm structure is preferred, any fluid collection pattern that collects fluid to a single point can be used.

Figure 2A:
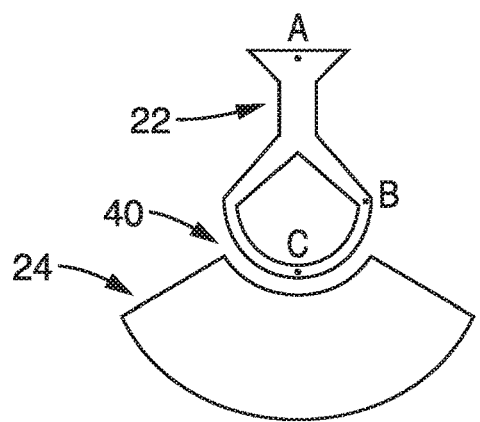
FIG. 2A is a schematic detail front view of the droplet formation and removal patterns of the wearable digital droplet flowmeter embodiment shown in FIG. 1A indicating progressing positions of the fluid flow path.

Attached to the fluid collection pattern 12 is a droplet counting structure 14 that has a microfluidic junction that includes a droplet formation pattern 22 and a droplet removal pattern 24, which are separated by a superhydrophobic gap 40 (see FIG. 2A). The droplet formation pattern 22 is typically made from the same hydrophilic material used to form the fluid collection pattern 12. The droplet formation pattern 22 also has an electrode 26 that is connected to a reversible circuit connector 28 with conductive threads or fine gauge wires 30 shown in dashed lines. The droplet formation pattern 22 is configured to form single drops at the gap between the droplet formation pattern 22 and the droplet removal pattern 24.

The droplet removal pattern 24 has a droplet receiver 32 that is made of hydrophilic material that is aligned across the superhydrophobic gap with the droplet formation pattern 22. In one embodiment, the droplet receiver 32 includes one or more projections into the gap that assist in bridge initiation.

The droplet removal pattern also has a second electrode 34 that is coupled to a second reversible circuit connector 36 with conductive threads or fine gauge wires 38 shown in dashed lines in FIG. 1A. The fluidic junction converts the continuous flow into discrete droplets with identical volume, from which the flow rate can be simply assessed by the digital counting circuitry (as the droplet number multiplied by the droplet volume).

The embodiment shown in FIG. 1A is a soft and breathable microflowmeter that can be simply fabricated by standard textile manufacturing techniques including laser-machining of the hydrophilic flow patterns on top of the superhydrophobic fabric and embroidering conductive sensing patterns and circuit connectors to the counting area.

The fabric-based DDF system with integrated real-time functions of fluid collection, droplet formation and digital counting that are all essential for wearable monitoring of perspiration. In particular, an array of ports 20 of various sizes or shapes can be cut open to the skin-contact side of the fabric, which can then be used to collect perspiration from the skin to the hydrophilic DDF network through the hydrophobic substrate. Sweat can therefore be directed through the pores from the back of the device (the skin contact-side) to the front hydrophilic fluidic patterns as illustrated in FIG. 1B.

Figure 2B:
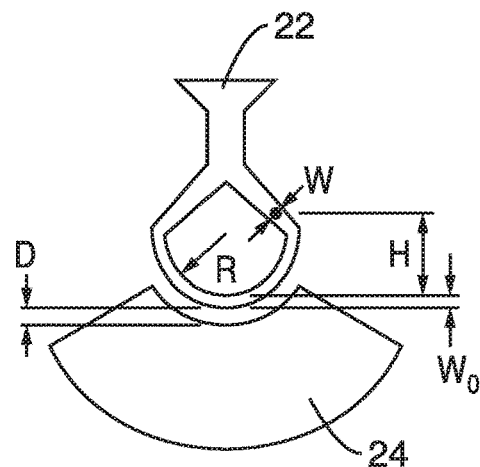
FIG. 2B is a schematic detail front view of the droplet formation and removal patterns of the wearable digital droplet flowmeter embodiment shown in FIG. 1A indicating dimensional variables for successful droplet generation and removal.
Figure 2C:
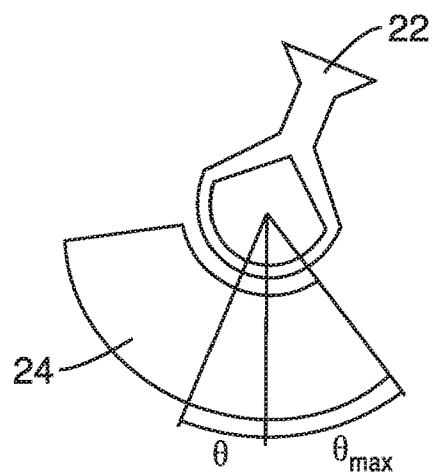
FIG. 2C is a schematic detail front view of the droplet formation and removal patterns of the wearable digital droplet flowmeter embodiment shown in FIG. 1A set at an angle.

Referring now to FIG. 2A, FIG. 2B and FIG. 2C, the droplet formation pattern 22 and droplet removal pattern of the droplet counting structure 14 are of the embodiment shown in FIG. 1A are illustrated. It can be seen that the structural design parameters of the microflowmeter, including geometrical designs (e.g., nozzle dimension, gap distance, channel width and depth), physical properties (e.g., surface tension), surface chemistry and energy (e.g., wettability), and fluid dynamics (e.g., flow rate, inlet and outlet pressure), can be optimized.

The fabric-based DDF platform in this embodiment is designed to collect and measure liquid flow using a wettability-contrast microfluidic network built on a fabric substrate. The droplet formation pattern 22 of the microjunction with the fluid collection pattern shown in FIG. 2A has a fluid flow path and geometry designed to form a droplet of a consistent size. The continuous stream of fluid from the fluid collectors is turned into a discrete digital droplet sequence, which can be easily detected and assessed by integrated electronic circuitry.

As the flow approaches the bottom of the collection pattern indicated at Point A of FIG. 2A, the hydrophilic path is divided and narrowed into two arms (Point B) so that the three-phase contact lines are pinned at the interface between the hydrophilic pattern and the hydrophobic substrate. The two arms are joined with an arcuate piece with a low point at Point C, where a droplet forms.

In principle, the narrower width of the flow path would result in a higher Laplace pressure. As can be seen in FIG. 2A, the channel width is reduced from Point A to Point B and then to Point C, the hydrostatic pressure decreases, but the Laplace pressure increases. The overall pressure (p), i.e., hydrostatic plus Laplace pressure, can be expressed as:

$$p = \frac{\gamma}{W} + \rho g H \cos\theta,$$

where $\rho$ and $\gamma$ represent the density and surface tension of the fluid, and W and H are the width and height of the pattern/channel, respectively. In addition, $\theta$ stands for the tilting angle, which influences the hydrostatic pressure.

The DDF platform is intended to work at various tilting angles (as large as $\pm 45°$) from vertical position when it is worn on a moving body surface, such as swinging limbs during exercise. This can be achieved by designing a semi-circular droplet formation loop (of $W_0$ in width and R in radius) surrounded by a dome-shaped droplet removal pattern with a separation of D, as shown in FIG. 2B.

As the structure rotates at various angles, there remains an identical path for droplets to be collected as shown in FIG. 2C. As can be seen, to establish a stable and continuous flow all the way from the fluidic transport network (Point A) to the droplet generation site (Point C), there should be continuous and positive driven pressure, i.e., the Laplace pressure plus the hydrostatic pressure at any point along the flow path (from A to C) should be greater than the Laplace pressure at Point C. This requirement produces a positive driven pressure for the flow and can be mathematically described as $$\Delta p = \left(\frac{\gamma}{W} + \rho g H \cos\theta\right) - \frac{\gamma}{W_0} > 0,$$

where H indicates the vertical height of the droplet position and W is the width of the bifurcation path. Accordingly, for a given pattern width $W_0$ of droplet formation loop, the width of the flow path at any height H should satisfy the condition $$W < \frac{1}{\frac{1}{W_0} - \frac{\rho g H \cos\theta}{\gamma}}$$

to ensure continuous flow to Point C of the formation loop that is illustrated in FIG. 2A.

Simulation results based on different values of H and $\theta$ demonstrated that a wider flow path requires a larger hydrostatic pressure/gravitational height to drive down the droplet for the same initial width ($W_0$=1 mm). Once the height goes beyond a threshold value, i.e., the hydrostatic pressure remains greater than the maximal Laplace pressure, the width of the fluidic path has no further restriction. Moreover, the increment in the titling angle would reduce the channel width at the same height.

The flow continuously accumulates and forms droplets on the collection pattern. As the droplet volume grows, it reaches the inverted dome-shaped hydrophilic removal pattern separated by a superhydrophobic gap 40 and is instantly removed by the strong capillarity.

In brief, the droplet removal pattern provides a simple means to transfer the droplets with a controlled volume. Without the removal pattern and the superhydrophobic gap 40, the droplet volume would be much larger and dependent on gravitational forces. As long as the droplet volume maintains a constant value of $V_0$, the flow rate (Q) can be quantitatively determined in a continuous manner through the measurement of the duration ($\Delta t_0$) between consecutive droplet removals, expressed as:

$$Q = \frac{\Delta V}{\Delta t} = \frac{n * V_0}{n * \Delta t_0} = \frac{V_0}{\Delta t_0}$$

In principle, a smaller droplet volume leads to a higher measurement precision. The resolution of the digital measurement of the DDF platform relies primarily on the smallest droplet volume ($V_0$) it can form. Small droplet formation can be advantageous for the following reasons: a) a shorter formation time is required to generate a droplet, which improves the response time and measurement resolution of the system; b) small droplet size is primarily determined by the capillarity and less influenced by gravitational and other body forces and the droplet geometry and volume can be more accurately defined by the DDF flow patterns. As the droplet volume determines the resolution of the digital flowmetry, it can be influenced by three geometric parameters: the separation distance (D) between the droplet collection and removal patterns, the radius (R) and the width (W) of the collection pattern of FIG. 2B.

The droplet is initially formed on the formation pattern due to its hydrophilic nature. As the fluid accumulates, the size of the droplet grows. After the droplet size exceeds the pattern width (W), the continuous size growth due to liquid accumulation allows the droplet surface to approach the droplet removal pattern that has a distance (D) away from the formation pattern. Therefore, the sum of the formation pattern width (W) and the separation distance (D) determines the final size of the droplet before it is removed. Smaller values of (W) and (D) lead to a smaller droplet volume and better resolution of the DDF system. The minimal resolution of the flow patterns with smooth line boundaries is preferably set at approximately 500 µm by the laser micromachining on the fabric materials. Therefore, the values of separation distance and the width of collection pattern can typically be as small as 500 µm for the DDF system.

Figure 3A:
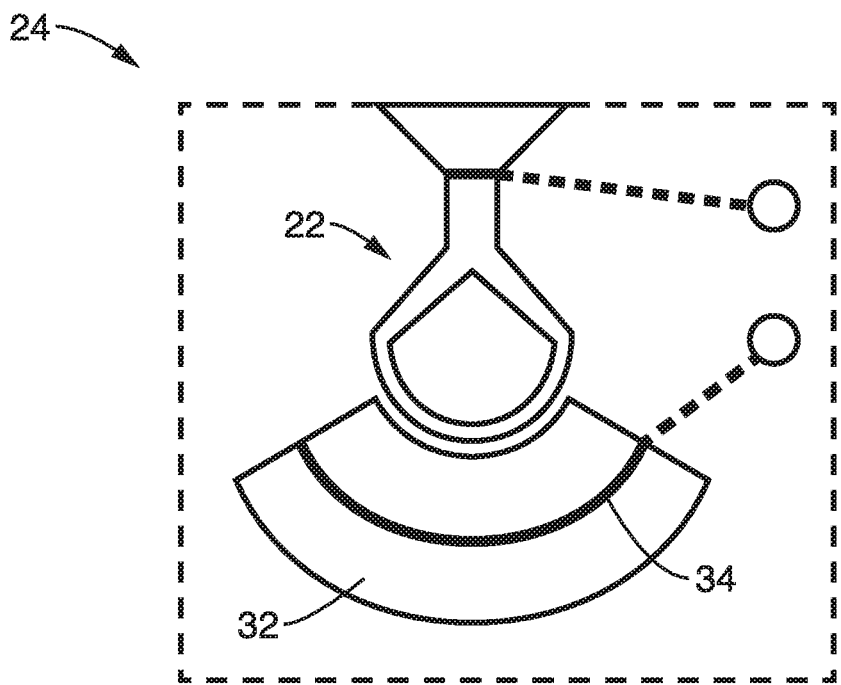
FIG. 3A is a schematic detail front view of the droplet formation and removal patterns of the wearable digital droplet flowmeter embodiment shown in FIG. 1A depicting the circuit in an open or high resistance state.
Figure 3B:
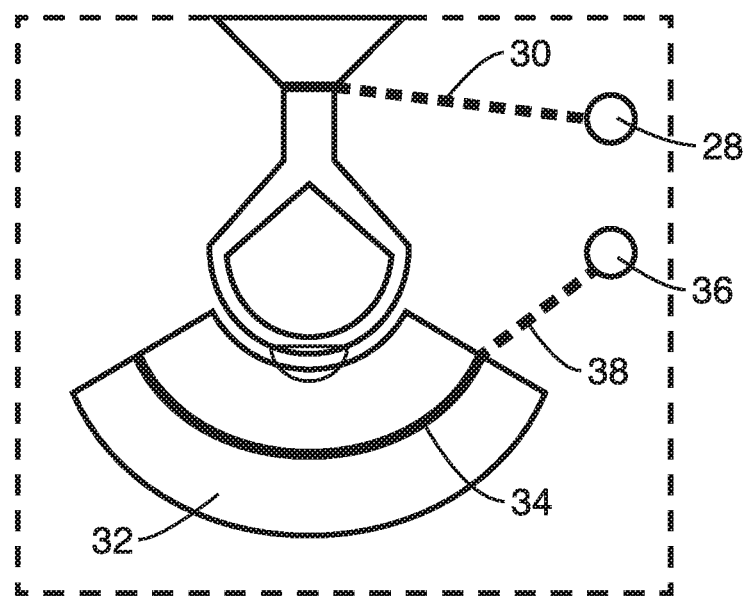
FIG. 3B is a schematic detail front view of the droplet formation and removal patterns of the wearable digital droplet flowmeter embodiment shown in FIG. 1A depicting the circuit in a closed or low resistance state.

A simple resistance-based counting circuit may be applied to the DDF according to the droplet formation and removal mechanism, where two electrically conductive threads are stitched inside the upper and lower hydrophilic patterns, as illustrated in FIG. 1A, FIG. 1B and FIG. 3A and FIG. 3B. As shown in FIG. 3A, prior to the contact of the droplet to the lower removal pattern 24, the electrical resistance between the top and bottom electrodes should be infinitely high (as an open-circuit state). Once the droplet reaches the removal pattern and bridges as seen in FIG. 3B, the ionic conductance inside the droplet would electrically connect both the upper and lower electrodes, which results in a connecting/low-resistance state. After the droplet removal by the droplet removal pattern 24, the circuit returns to its open-circuit state shown in FIG. 3A.

Using a standard ADC circuitry, the repetitive process of droplet formation and removal can be converted to a series of pulsation patterns in the resistance measurement, which can be digitally recognized using a DSP algorithm, for example. Assuming the drop factor is fixed as a constant, the infusion rate is monotonically proportional to the dripping frequency that can be simply computed by counting droplet numbers in a defined time period.

Figure 4A:
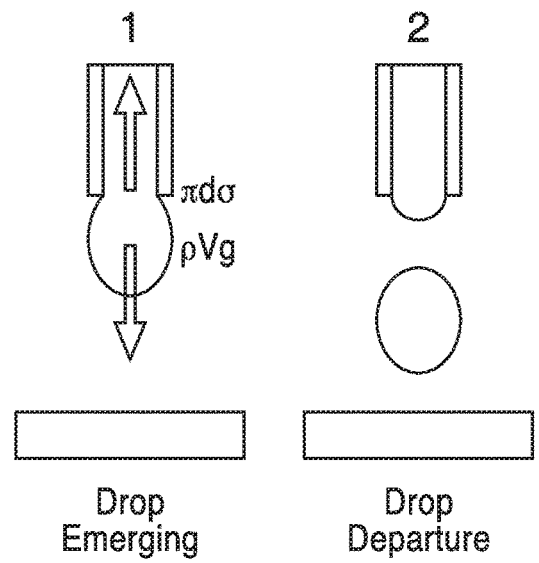
FIG. 4A is a schematic side view of a nozzle of a conventional gravity drip system mechanism showing drop emergence and drop departure.
Figure 4B:
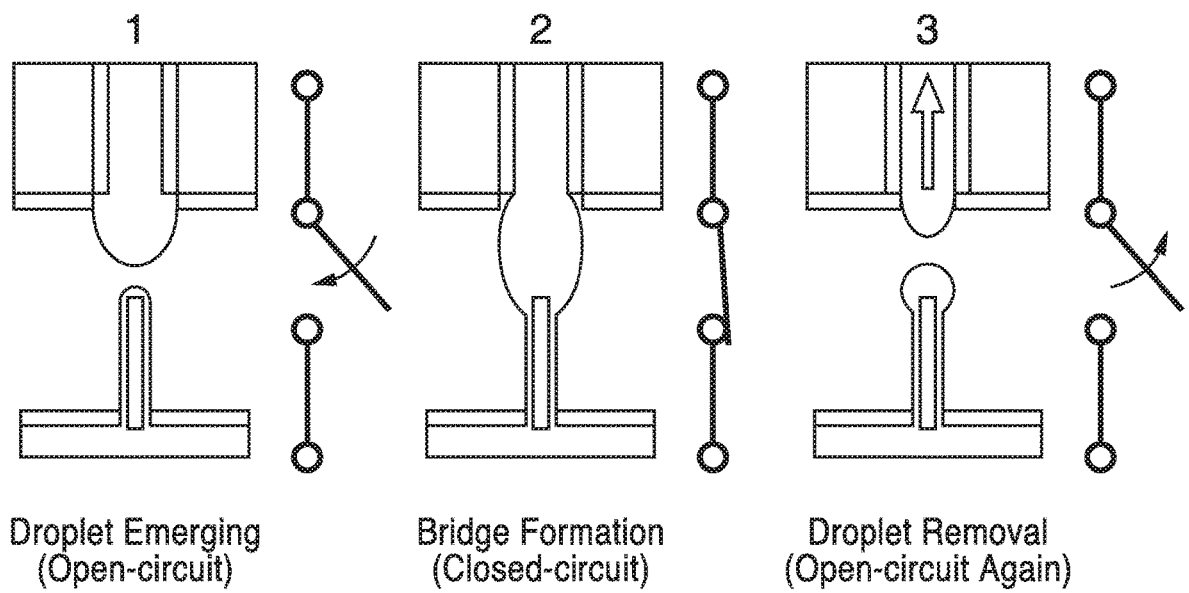
FIG. 4B is a schematic view of a nozzle and receiver of a digital droplet microflowmetry system mechanism showing droplet emergence, bridge formation and droplet removal.

The droplet forming and counting mechanism of the DDF platform is described and compared to the classic gravity drip system in FIG. 4A and FIG. 4B. In comparison to a conventional gravity drip system, DDF flowmetry: 1) can significantly reduce the droplet size to a nanoliter or even picoliter volumes, i.e., increasing the drop factor, by manipulating the surface tension and surface energy; 2) decouples the droplet volume from gravitational and inertia forces; and 3) utilizes interfacial instability to establish a simple droplet-counting mechanism to measure ultralow flow rates electronically.

In the conventional gravity drip shown in FIG. 4A, droplets in condition 1 are under the influence of both gravitational ($\rho V g$) and surface tension forces ($\pi d \sigma$) in addition to the nozzle diameters. Balancing gravitational force and surface tension of a droplet produces a critical droplet volume, approximated as $V = \pi d \sigma / \rho g$, where d stands for the nozzle diameter, $\sigma$ and $\rho$ are surface tension and the density of the working fluid, respectively. Ultimately, the formed drop separates from the nozzle as shown in condition 2 of FIG. 4A.

By comparison, the DDF 3D mechanism illustrated in FIG. 4B completely relies on surface forces, instead of body forces, to facilitate the droplet formation and removal, which works at a higher efficiency and accuracy in smaller scales. Specifically, the dimensionless Bond number $B_0 \equiv (l/a)$ compares the dominance of body force (gravity) and surface force (capillarity), where l is the characteristic length and a represents capillary length that follows $a \equiv (2\sigma/\rho g)^{1/2}$. The typical capillary length of water is around 3.8 mm at a room conditions, which is equivalent to a spherical droplet size of 29 µL. Thus, as the droplet size is further reduced below the capillary length (i.e., $B_0 < 1$), the surface forces become dominant.

The electrical measurement mechanism, which detects the transient formation of an electrically conductive liquid bridge as an electrical switching event is also shown in FIG. 4B. A three-step mechanism of 1) droplet emergence; 2) the formation of a liquid bridge (the closed-circuit state); and 3) the breakup of the bridge (the open-circuit state) is shown in FIG. 4B. The duration of the formed bridge lasts only a few milliseconds.

Droplet emergence of the first step in FIG. 4B preferably takes place in a very hydrophilic droplet-collecting site in a precisely controlled distance from the droplet forming pattern or nozzle, while the surrounding area of the pattern or nozzle is very hydrophobic. Consequently, the droplet formation process will be confined within the inner diameter of the nozzle due to the wettability contrast between the inner and outer surfaces of the nozzle. The circuit is open as shown in FIG. 4B.

As the droplet grows in step 2 of FIG. 4B, it approaches to the hydrophilic collecting receiver opposite the nozzle or pattern. Upon reaching the collecting receiver surface, the droplet will first make a physical contact with the collecting surface and then form a liquid bridge between the surface and the nozzle or pattern. In the embodiment shown, a point of first contact of the droplet with the receiver is an optional vertical post or tip with dimensions providing design control over the drop size before bridging. A closed-circuit path can be established through the transient liquid bridge, which can be utilized for simple electronic detection purposes.

The overall surface energy of the system of the bridge is minimized by spreading onto the very hydrophilic area, resulting in breakage of the liquid bridge. In one embodiment, the receiver includes one or more drains for quickly removing collected fluid from the receiver. According to Rayleigh instability theory, a stable liquid bridge pinned on a nozzle can be maintained in a static condition, if the gap distance δ and liquid bridge radius $R_L$ satisfy the following condition $\delta/R_L < 2\pi$. In other words, a liquid bridge that does not match this condition would experience spontaneous breakage due to interfacial instability as shown in step 3 of FIG. 4B. Importantly, the ejected droplet volume ($V_d$) in DDF platform in step 3 follows $V_d = V_0 + \dot{m}t$, where $V_0$ is the droplet volume removed from the nozzle towards the collecting surface at the bridge breakage, $\dot{m}$ is the mass flow rate, and t stands for the duration of liquid bridge.

Breaking of the fluid bridge at step 3 of FIG. 4B also results the opening of the electrical circuit that is detected and completes the counting event.

Figure 5:
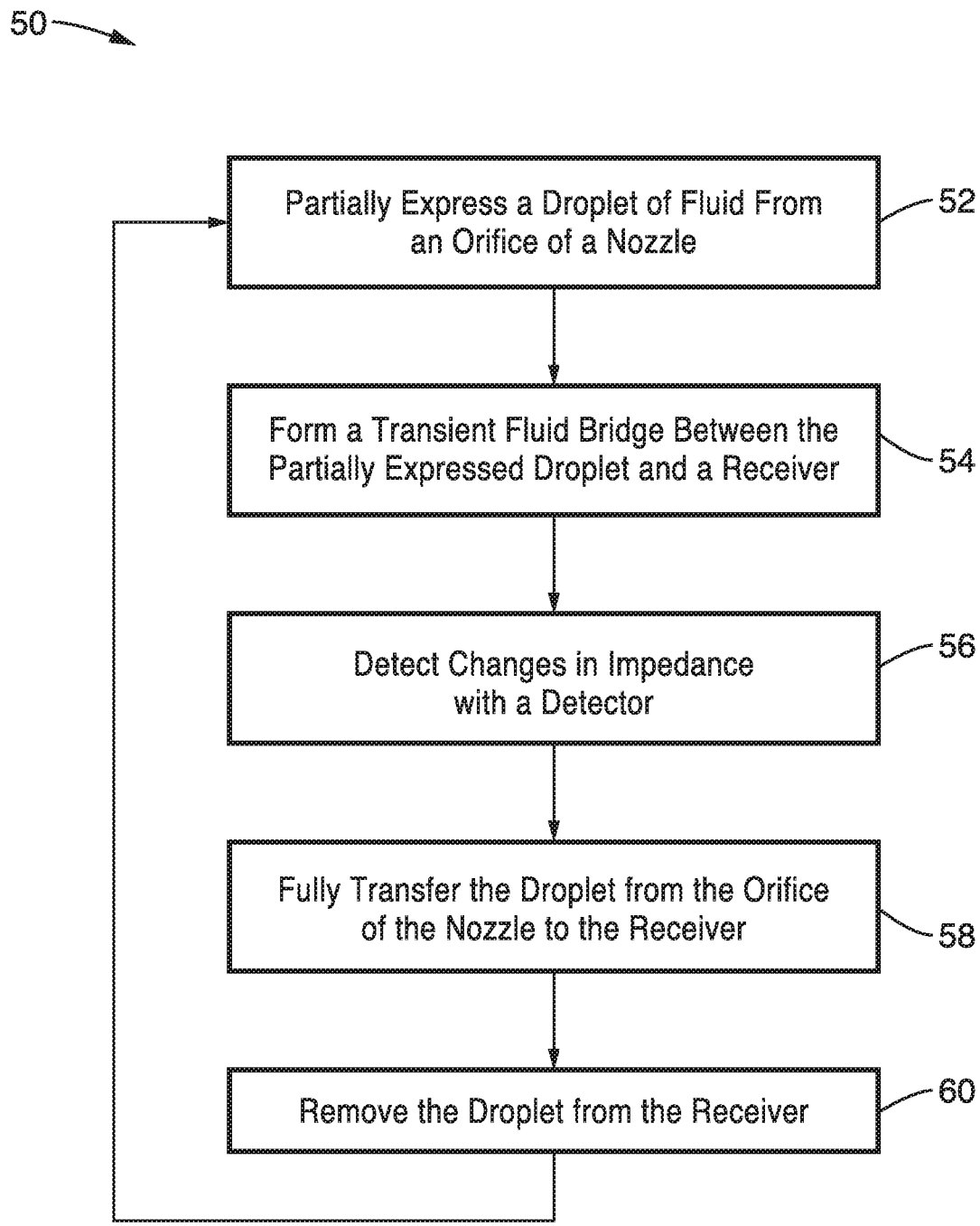
FIG. 5 is a functional block diagram of a method for measuring ultralow fluid flow rates according to one embodiment of the technology.

One method 50 for digital droplet flowmetry is set forth in FIG. 5. At block 52, a droplet of fluid is expressed from a nozzle or droplet formation pattern and moves toward a hydrophilic receiver oriented across a hydrophobic or superhydrophobic gap.

A transient fluid bridge between the nozzle and the receiver is established at block 54 of FIG. 5. The receiver is preferably made from a hydrophilic material. In one embodiment, the receiver has an arcuate surface or other shape that corresponds to the shape of the droplet formation pattern. In another embodiment, the droplet receiver has a generally horizontal surface and a vertical member aligned with a nozzle that encounters the expressed droplet first. The bridging duration (frequency) and droplet volume (drop factor) can be controlled and optimized by geometrical designs and spacing as well as the chemical and physical properties of the collected fluid.

At block 56 of FIG. 5, changes in impedance are detected with a detector. The formation of the transient fluid bridge allows the detection of changes in impedance between the droplet formation structure electrodes and the droplet receiving structure electrodes. Simple acquisition circuitry detects the interfacial rupturing events by measuring AC conductance of the fluid, during which dramatic changes in electrical impedance are triggered at block 56.

The impedance detection circuitry at block 56 can include computer control programming, processing, transmission and recordation features. Detector programming may process and record droplet volume, flow rates etc. The detector may also have a display for viewing the captured and recorded data graphically. The detector may also transmit data to a remote location for processing, recording and modelling in one embodiment. A volume of the droplet from the nozzle is fully transferred to the receiver at block 58 with the breaking of the transient fluid bridge. At the same time, the electrical circuit is opened with the breaking of the transient fluid.

At block 60, the system resets with the whole or partial removal of the received droplet and the concurrent expression of a new droplet from the orifice of the nozzle of drop formation pattern at block 52. The fluids from received droplet may also drained and collected for further analysis at block 60. In one embodiment, the composition of the removed droplets is analyzed with one or more sensors or tests. In another embodiment, the droplet removal pattern has a lab-on-yarn or lab-on-paper or lab-on-film type sensor integrated in the removal pattern.

Figure 6:
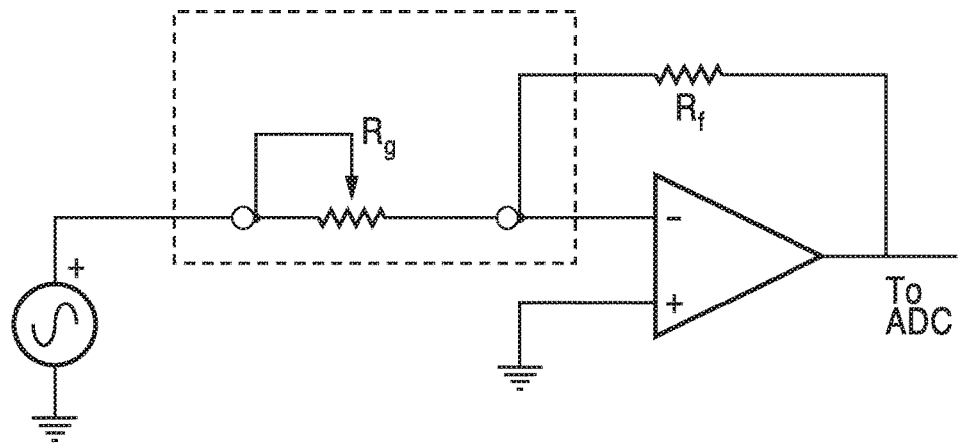
FIG. 6 is a schematic diagram of a simple circuit that can be used for droplet counting according to one embodiment of the technology.

A simple acquisition circuit embodiment is shown in FIG. 6. Using a standard analog-to-digital (ADC) circuitry, the repetitive process of droplet formation and removal shown in FIG. 5 can be converted to a series of pulsation patterns in the impedance measurements of the detector, which can be digitally recognized with a digital signal processing (DSP) algorithm. This type of circuitry is preferred because of its extremely low power consumption that allows for the creation of completely passive and wireless circuits for special applications.

Figure 7:
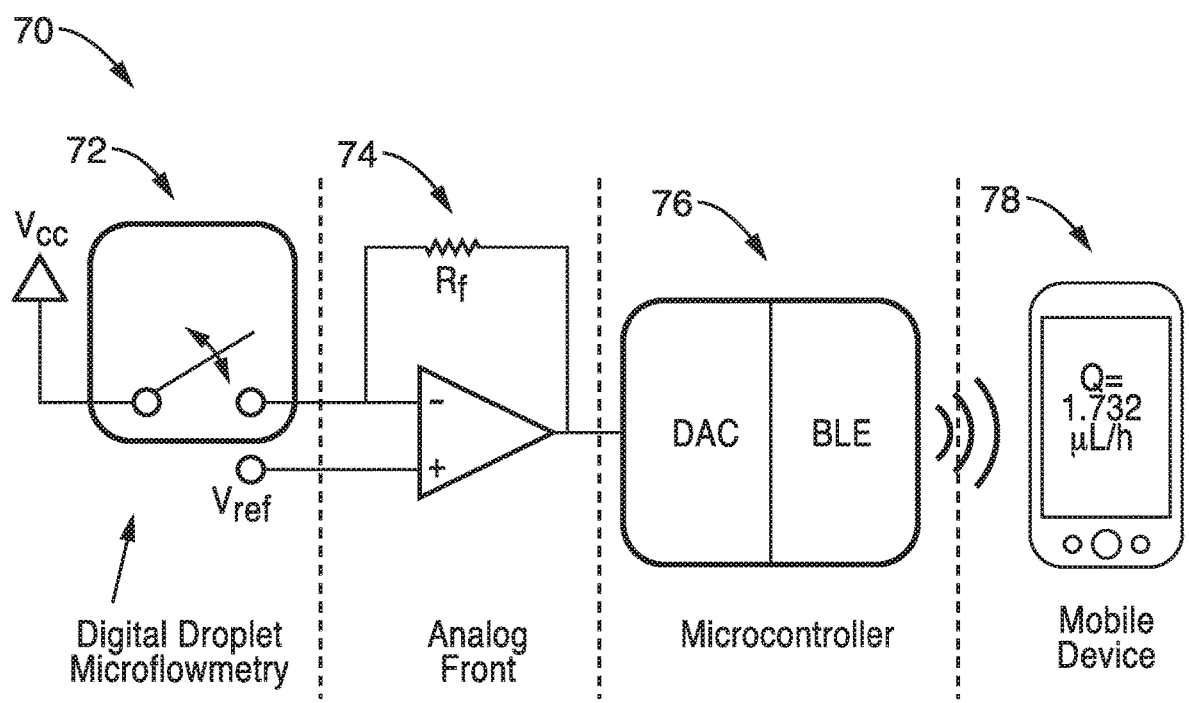
FIG. 7 is a schematic diagram of an active wireless measurement system including the digital droplet microflowmeter, analog front, Bluetooth enabled microcontroller and a mobile terminal according to one embodiment of the technology.

Accordingly, both active and passive wireless measurement systems can be implemented. An active wireless embodiment 70 of the technology is shown in FIG. 7. The active wireless acquisition system 70 has data transmission circuitry, real-time processing and a graphical user interface on a mobile terminal that is programmed for real-time data collection and analysis.

The system 70 embodiment shown schematically in FIG. 7 has four system modules. The first module 72 is the digital droplet microflowmetry module that is based on detecting the closed-circuit state (low-impedance) during the transient liquid bridge formation described previously.

The second module 74 is an analog front coupled to the detector of the first module. These modules can be combined as shown in the circuit of FIG. 6.

The third module 76 is a microcontroller and transmitter module. The analog front module 74 is coupled to an analog digital converter, microcontroller and transmitter such as a Bluetooth-enabled microcontroller or Wi-Fi transmitter. In the active system, a Bluetooth low-energy (BLE) module can be used to transmit the data wirelessly to a mobile device. In the passive system, a wireless LC transponder approach can be used to count the droplet number through an inductive linkage between the sensing loop and the external readout circuitry, which eliminates the power requirement on the device. In another embodiment, the droplet counting and integrated readout and transmission circuitry of the first three modules fabricated on a single printed circuit board (PCB).

The fourth module 78 is a mobile device such as a mobile telephone that is wireless connected to the droplet counting modules. A mobile terminal provides real-time processing, data storage, a display as well as a user interface. In one embodiment, the device is configured for connection to the Internet through Wi-Fi transmissions.

The technology described herein may be better understood with reference to the accompanying examples, which are intended for purposes of illustration only and should not be construed as in any sense limiting the scope of the technology described herein as defined in the claims appended hereto.

Example 1

In order to demonstrate the functionality and operational principles of the digital droplet microflowmetry platform and methods, fabric-based digital droplet flowmeters were fabricated and evaluated. The method of fabrication of the devices is generally depicted in FIG. 8A to FIG. 8F which illustrates an embodiment of the fabrication process for wearable DDF system on a textile.

As seen in FIG. 8A to FIG. 8F, the flowmeter is fabricated in two halves that are joined together to complete the device. The bottom half is formed in steps depicted in FIG. 8A and FIG. 8B and the top half is formed in the steps depicted in FIG. 8C and FIG. 8D. The two halves are joined together as shown in FIG. 8E and removed from solid supports to complete the structure as shown in the step depicted in FIG. 8F.

Initially, a superhydrophobic (SH) fabric 100 was prepared by treating an off-the-shelf polyester knitted fabric (weight 172 g/m$^2$) with a commercially available fluoropolymer-based water-repellent coating (Aqua Armor), which was said to provide superior waterproofing protection for outdoor clothing and gear. In principle, however, the fabric 102 can be treated by most of commercial hydrophobic coatings available in the market. The treated fabric 102 was subsequently dried in a heated oven at 80° C. for 30 minutes and placed on a solid support 104 shown in FIG. 8A. The thermal treatment allows the bonding of the waterproofing formula to the fibrous structures of the fabric, leading to a durable protection.

Through-holes 106 or similar openings were then cut in the SH fabric layer 102 to complete the first half as shown in FIG. 8B.

The hydrophilic fluidic patterns of the second half illustrated in FIG. 8C and FIG. 8D were fabricated using non-woven fabric 108 made of cellulose/polyester blend (TX629, Texwipe) or nylon fabric that was placed on a solid support 110 to provide a planar surface for device fabrication. Capillarity was employed to temporarily attach the hydrophilic substrate 108 to the solid support 110 by wetting. The Texwipe fabric 108, with a thickness of 130 µm, provided high-level hydrophilicity to initiate the collection flow, but retained a minimal amount of fluid inside their porous structure. A double-sided tape (3M™ 467 MP) layer 112 was applied to the top surface of the non-woven fabric layer 108. The double-sided tape was used as an adhesion layer to bond the hydrophilic fluidic layer 108 to the superhydrophobic (SH) fabric 102 illustrated in FIG. 8C.

A laser-engraving machine (VLS 2.30, Universal Laser Systems) was applied to pattern the dedicated fluidic channels 116 and through-holes on all the layers of both the first and second halves.

In the following step shown in FIG. 8D, the hydrophilic non-woven substrate 108 and the double-sided tape layer 112 were trimmed into the selected microfluidic patterns.

Finally, the top hydrophilic fluidic layer and the bottom SH substrate were aligned and bonded together by applying a uniform compression pressure through a custom roller as illustrated in FIG. 8E, followed by releasing from the solid supports from the joined halves in the step depicted in FIG. 8F. The combination of the two halves formed channels 116 in the completed structure.

Two types of devices were fabricated for evaluation. The Type 1 DDF platform was fabricated using the non-woven Texwipe fabric 108 with a sweat-collecting area of 18 cm$^2$ (of which 61% hydrophilic area) and the Type 2 DDF was fabricated using nylon fabric 108 with a collecting area of 9 cm$^2$ (of which 50% hydrophilic area). Type 1 DDF devices were used in all the experiments, while the Type 2 DDF platforms were only applied to the flow rate measurements of Example 2 to study the influence of evaporation.

Example 2

The resolution and dimensions of the interfacial microfluidics of the fabric-based digital droplet flowmeters that were produced were evaluated. For fluidic characterization, device patterns with different design parameters were evaluated for their influences on the DDF performance including volume variation of individual droplets.

The fabricated patterns were primed by a simulated saline solution (i.e., 0.5% sodium chloride-containing aqueous solution) and droplets were consecutively dispensed onto the DDF device by a micropipette. Pictures taken from a digital camera mounted on a stereoscope (Canon Rebel T3) were used to measure the geometric dimensions. Based on the characterization results, an optimal DDF pattern was implemented to measure various flow rates generated by a syringe pump, and the accuracy of the flow rate measurement was calculated by comparing with the referenced flow rate set by a syringe pump (KDS100, KD Scientific).

A simplified setup for artificial sweat perspiration was used. A 1 mL syringe was connected to a pump and the liquids were pumped and directly dispensed through a plastic pipette tip placed close to the center of the fluid collecting pattern. All the characterization measurements were repeated and measured at least three times, and the mean values and standard deviations were calculated for each measurement.

Channel widths of 200 µm, 300 µm, 400 µm 500 µm and 600 µm formed with laser micromachining were compared to determine the pattern resolution of the fabric materials (e.g., TX629, Texwipe). It was observed that the pattern width below 300 µm can result in irregular and even discontinued patterns in the flow path. In contrast, the pattern widths above 500 µm demonstrated flow paths with relatively smooth boundaries. The boundary smoothness can be important, as irregular defects (e.g., spikes or dents) may cause considerable errors in the flow rate measurement due to non-uniformity in the formation and collection of the droplets. Therefore, a resolution at 500 µm was set as a minimum pattern width of the DDF device on the non-woven fabric.

The range of the measurable flow rates can be influenced by the geometric parameters and the operational conditions of the system. To determine the maximum flow rate of the DDF system, the width of the flow path can play an important role. For a given width of hydrophilic pattern, a rising flow rate can lead to a thicker and more curved gas-liquid interface, which results in a greater value of the local Laplace pressure. However, such an increase in the induced Laplace pressure at the point of droplet formation (e.g. Point C in FIG. 2A) is more substantial than that of the upstream locations due to the accumulation of fluid at Point C. This effect would reduce the net driven pressure of the flow for droplet formation. As the flow rate reaches a critical point, the driven pressure approaches zero ($\Delta p=0$) with no continuous droplet formation, which defines the maximal flow rate of the platform.

Since the maximum flow rate is dependent on the width of the hydrophilic pattern, various pattern widths of 0.7 mm, 0.8 mm, 0.9 mm, 1.0 mm and 1.1 mm were investigated. It was observed that the maximum flow rate of the channel increased from 9.7 µL/min to 245.8 µL/min in an exponential manner as the pattern/channel width increased from 0.7 mm to 1.1 mm. This trend indicated that a small change in the pattern/channel width can have a strong influence on the maximum transport rate of the system.

In addition to the maximum flow rate, the minimum measurable flow rate of the DDF system can be directly affected by evaporation if the system adopts an open interfacial microfluidic platform. When the flow rate is close to or even smaller than the evaporation rate, the measurement accuracy drastically dropped. The inaccuracy is mainly caused by evaporation which becomes manifest at very low flow rates.

To improve the measurement range of the flow rates, the evaporation over the wetted area of the device should be reduced. This may be accomplished by one of the following design strategies: 1) decreasing the width of the branched hydrophilic flow paths (i.e., non-woven hydrophilic fabric layer) while keeping the overall area the same or 2) enclosing the branched hydrophilic flow paths and therefore turning the major part of the surface microflow into a microchannel, by substantially compromising the flow conductance. The first strategy was adopted without compromising the self-driven flow. The minimal flow rate was measured at around 7 µL/min experimentally.

Furthermore, the influence of the radius of the droplet formation pattern shown in FIG. 2B was evaluated. Droplets of a fixed volume (6 µL) were evaluated from formation patterns of different radii (i.e., 2.5 mm, 3.5 mm and 5 mm). It was observed that the droplet tends to protrude downwards when it is formed on the hydrophilic pattern of a larger radius. This can be explained by the spontaneous minimization of liquid surface energy in open microfluidics, where the surface tension dominates over the gravitational force. For a fixed volume, the liquid droplet changes its shape to maintain the most stable state that requires the lowest surface energy.

In the case of a highly curved hydrophilic pattern (R<2.5 mm), a liquid bridge is formed over the curvature to stabilize the droplet by its own surface tension, which holds the droplet upward. However, if the hydrophilic pattern is less curved (R>4 mm), the same tension on the liquid generates a weaker lift, and more droplet volume is suspending downwards. In brief, droplets passing a hydrophilic path with a greater radius of curvature can be removed faster. Given a fixed line width (W=1 mm), the radius of the collection path increases from 2.5 mm to 5 mm at a 0.5 mm interval, the corresponding protrusion length rises from 350 µm (at 2.5 mm in radius) to 850 µm (at 5 mm in radius) for the same size of droplet (6 µL). Therefore, a larger radius of the droplet formation pattern is preferred in generating a smaller droplet volume and leading to a higher resolution of flowmeter design.

Example 3

To further demonstrate the fabric-based digital droplet flowmeter platform, the fabricated devices were attached to the upper arm of a mannequin as a demonstration of wearable perspiration monitoring. Human perspiration rates can range significantly from 100 g/m$^2$ h to 1700 g/m$^2$ h for various body sections during exercise process in moderately warm conditions (25° C., 50% relative humidity, 2 m/s air velocity), in which the perspiration rates were averaged among a group of human subjects. The DDF devices were designed to be primarily applied to the body areas in athletes that had high density of sweat glands and high perspiration rates, such as the foreheads, the upper backs and the shoulders. The sweat rate of shoulder can go from 12 µL/min to 30 µL/min over an 18 cm$^2$ area. With the same covering area, the sweat rate of foreheads was in the range of 29 µL/min to 102 µL/min while that of the upper backs was in the range of 17 µL/min to 46 µL/min.

The fluidic collection network of the DDF was designed to cover a square area of 18 cm$^2$ on the upper arm. The droplet counting was carried out in the same way through the snapping circuit interface. As can be seen, the fabric-based DDF is flexible and can be worn comfortably on the upper arm or other part of the body to simulate the case on real objects. In such a way, the DDF device enables accurate assessment of the simulated perspiration rates in a completely wearable fashion.

The performance of the wearable DDF device on the mannequin was demonstrated using a syringe pump filled with a simulated saline solution (i.e., 0.5% sodium chloride-containing aqueous solution). The syringe pump rate was set to generate a series of different simulated perspiration rates (each for 4 min) with a staircase ramping up phase from 16.7 µL/min to 66.7 µL/min and a similar ramping down phase to 25 µL/min. The DDF system was initiated to count the droplets as the flow path was primed.

The DDF apparatus responded quickly to the rate change of the injected flow and the measured flow rates were correlated well with the actual injection rates with variations in the range of 0.2-6.9% for all the measured points. The measurement variations can be attributed to the flexible air-liquid interface presented along the drainage path due to the change of the flow rate (similar to capacitive elements in an electronic circuit). In brief, the measurement results have demonstrated the capacity of the DDF system to provide real-time continuous monitoring of perspiration flow using the principle of droplet formation and collection.

Example 4

The flow-rate measurement circuitry of the fabric-based digital droplet flowmeter platform was evaluated. The embroidered circuit patterns utilized commercially available silver-plated Nylon threads (LessEMF). The conductive threads came with reasonable electrical conductivity (<2 kΩ/m) and were manually stitched and connected to the droplet generation and removal patterns, respectively. On the opposite end, the conductive patterns were connected to standard metal snap buttons (with 5 mm in diameter) to interface with the external circuitry. Specifically, the female piece was fixed onto the SH fabric by the conductive threads, while the male end was soldered with electrical wiring, which allowed the processing circuitry to be reversibly attached to the wearable DDF pattern. Furthermore, a signal acquisition, display and analysis system was built by using National Instrument data acquisition and LabVIEW system. The measurement data were sampled and transmitted at 100 kHz for real-time droplet counting.

The flexible DDF device collected and digitized the continuous flow into small fixed-volume droplets, and the droplet removal process could be detected by a simple resistance-measuring circuitry as illustrated in FIG. 7. By wiring the two conductive electrodes embedded in the droplet collection and removal patterns with the external circuitry through reversible snap connectors (FIG. 1A), the resistance change between the two electrodes can be closely tracked in real time. For most of the time, the measuring circuitry stays at a high-impedance mode, as the collection and removal patterns are not connected either fluidically or electrically. Once the growing droplet reaches the removal pattern, it suddenly triggers a low-resistance state by bridging the two patterns electrically, resulting in a drastic change in the resistive value.

Both Type 1 and Type 2 DDF devices were used in the flow rate measurements, while Type 2 devices were primarily applied to study the influence of evaporation. Continuous resistive recordings of the droplet counting structure of Type 1 DDF devices at two different flow rates were recorded. At a flow rate of 66.7 µL/min, droplet formation and removal were triggered around every 7 seconds. As the flow rate was reduced by half (33.3 µL/min), the duration between two droplet removals becomes 14 seconds.

Importantly, it was observed that once the growing droplet reaches the removal pattern, the measurement circuit would turn onto a low-resistance state immediately, followed by returning to a high impedance mode after less than 40 milliseconds. Compared with the timescale of the droplet formation, the short duration of the droplet removal process can be negligible, and would have a minimal effect on the flow rate measurement.

The total number of droplets measured by the circuitry were counted as the flow rate increased from 25 to 67 µL/min with 8.3 µL/min intervals (for Type 1 DDF) and from 3.3 µL/min to 33 µL/min with 3.3 µL/min intervals (for Type 2 DDF) for each 2 minute duration.

As expected, it followed a highly linear relationship with the flow rate with a correlation coefficient of 0.9947 for Type 1 DDF and 0.9997 for Type 2 DDF devices, which again validates the DDF measurement approach. In addition, according to the measurement, the average droplet volume equals to 7.1 µL for Type 1 DDF and 6.6 µL for Type 2 DDF.

Notably, a clear deviation was observed between the measured droplet number and the actual inflow rate at i.e., 25 µL/min for Type 1 DDF and 3.3 µL/min for Type 2 DDF. This may be due to the fact that the evaporation rate at a low flow rate becomes significant and reduces the measured flow rate by the DDF system. Accordingly, the device with a smaller wetting surface can measure the smallest flow rate around 7 µL/min (Type 2 DDF), as compared to the larger counterpart only capable of assessing a minimal flow rate around 25 µL/min (Type 1 DDF).

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

From the description herein, it will be appreciated that that the present disclosure encompasses multiple embodiments which include, but are not limited to, the following:

1. A two-dimensional microflowmeter apparatus, comprising: (a) a hydrophobic base with a top surface and a bottom surface; (b) a first hydrophilic fluid flow structure disposed on the top surface of the hydrophobic base; (c) a first conductor mounted to the first fluid flow structure; (d) a second hydrophilic fluid flow structure adjacent to the first hydrophilic fluid flow structure, the structures separated by a gap; (e) a second conductor mounted to the second fluid flow structure; and (f) a controller coupled to the first and second conductors configured to sense a change in impedance between conductors; (g) wherein a change in impedance is detected by the controller from the formation of a transient fluid bridge between the first and second hydrophilic fluid flow structures.

2. The apparatus of any preceding or following embodiment, wherein the first hydrophilic fluid flow structure comprises a fluid collection pattern fluidly coupled to a droplet formation pattern.

3. The apparatus of any preceding or following embodiment, wherein the droplet formation pattern comprises: an arcuate droplet forming member; and a first leg and a second leg, each leg fluidly coupled at one end to the fluid collection pattern and to an end of the arcuate droplet forming member at the other end.

4. The apparatus of any preceding or following embodiment, wherein the second hydrophilic fluid flow structure comprises a droplet receiving pattern and a fluid removal pattern.

5. The apparatus of any preceding or following embodiment, wherein the second hydrophilic fluid flow structure comprises: a droplet receiving pattern with an arcuate surface that parallels an arcuate surface of the droplet forming member separated by the gap; and a fluid removal pattern joined to the droplet receiving pattern.

6. The apparatus of any preceding or following embodiment, wherein the base beneath the first hydrophilic fluid flow structure and the second hydrophilic fluid flow structure separated by a gap comprises a superhydrophobic top surface.

7. The apparatus of any preceding or following embodiment: wherein the hydrophobic porous base with a top surface and a bottom surface has a plurality of through holes; and wherein the first hydrophilic structure is disposed on the top surface of the base over the through holes.

8. The apparatus of any preceding or following embodiment, wherein the droplet receiving pattern further comprises a bridge initiation projection with an orientation perpendicular to the droplet forming pattern.

9. The apparatus of any preceding or following embodiment, further comprising: a communications link coupled to the controller; and a wireless computation device in communication with the controller through the communications link.

10. A digital droplet microflowmeter apparatus, comprising: (a) a droplet nozzle with a superhydrophobic outer surface, one or more fluid channels and at least one orifice in the nozzle outer surface; (b) a first electrode operably coupled to the droplet nozzle; (c) a droplet receiver with a hydrophilic outer surface; and (d) a second electrode operably coupled with the droplet receiver; (e) wherein a transient fluid bridge is formed between the droplet nozzle and the droplet receiver from fluid emerging from the orifice of the droplet nozzle closing the circuit between the first and second electrodes.

11. The apparatus of any preceding or following embodiment, the droplet receiver further comprising: a post with a hydrophilic surface oriented perpendicularly to a planar outer surface of the droplet receiver.

12. The apparatus of any preceding or following embodiment, the droplet receiver further comprising: a plurality of drains oriented opposite of the orifice of the droplet nozzle.

13. The apparatus of any preceding or following embodiment, further comprising: a controller configured to receive signals from the first and second electrodes; and a display connected to the controller.

14. The apparatus of any preceding or following embodiment, further comprising: a controller configured to receive signals from the first and second electrodes; a communications link coupled to the controller; a wireless computation device in communication with the controller through the communications link; and a display connected to the wireless computation device.

15. The apparatus of any preceding or following embodiment, wherein the communications link comprises a Bluetooth communications link and the wireless computation device comprises a smart telephone.

16. The apparatus of any preceding or following embodiment, the wireless computation device further comprising: (a) a processor; and (b) a non-transitory memory storing instructions executable by the processor; (c) wherein the instructions, when executed by the processor, perform steps comprising: (i) receiving transmitted signals from a controller of detected changes in impedance between electrodes upon formation of the transient fluid bridge between the droplet nozzle and the droplet receiver; (ii) calculating a rate of droplet flow; (iii) calculating flow volume; and (iv) displaying the volume and rate of droplet flow on the display.

17. The apparatus of any preceding or following embodiment, wherein the instructions when executed by the processor further perform steps comprising: recording calculated flow rates and flow volumes over time.

18. A method for measuring ultralow fluid flow rates, the method comprising: (a) partially expressing a droplet of fluid from an orifice of a nozzle; (b) forming a transient fluid bridge between the partially expressed droplet and a droplet receiver; (c) detecting changes in impedance with a detector; (d) fully transferring the droplet from the orifice of the nozzle to the receiver; and (e) removing the droplet from the receiver.

19. The method of any preceding or following embodiment, further comprising: producing a signal from the detector; transmitting produced signals from the detector to a wireless computation device; calculating a rate of droplet flow; calculating droplet flow volume; and displaying the calculated flow rate and flow volume on a display.

20. The method of any preceding or following embodiment, further comprising: recording calculated flow rates and flow volumes over time.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A two-dimensional microflowmeter apparatus, comprising:
    (a) a hydrophobic base with a top surface and a bottom surface;
    (b) a first hydrophilic fluid flow structure disposed on said top surface of the hydrophobic base;
    (c) a first conductor mounted to the first hydrophilic fluid flow structure;
    (d) a second hydrophilic fluid flow structure adjacent to the first hydrophilic fluid flow structure, said first and second hydrophilic flow structures separated by a gap;
    (e) a second conductor mounted to the second hydrophilic fluid flow structure; and
    (f) a controller coupled to the first and second conductors configured to sense a change in impedance between conductors;

(g) wherein a change in impedance is detected by the controller from the formation of a transient fluid bridge between the first and second hydrophilic fluid flow structures.

2. The apparatus of claim 1, wherein said first hydrophilic fluid flow structure comprises a fluid collection pattern fluidly coupled to a droplet formation pattern.

3. The apparatus of claim 2, wherein said droplet formation pattern comprises:
an arcuate droplet forming member; and
a first leg and a second leg, each leg fluidly coupled at one end to the fluid collection pattern and to an end of the arcuate droplet forming member at the other end of the leg.

4. The apparatus of claim 3, wherein said second hydrophilic fluid flow structure comprises:
a droplet removal pattern with an arcuate surface that parallels an arcuate surface of said droplet forming member and wherein said arcuate surfaces are separated by said gap; and
a droplet receiver.

5. The apparatus of claim 2, wherein said second hydrophilic fluid flow structure comprises a droplet removal pattern and a droplet receiver.

6. The apparatus of claim 5, wherein said droplet receiver further comprises a bridge initiation projection with an orientation perpendicular to the droplet formation pattern.

7. The apparatus of claim 1, wherein said hydrophobic base comprises a superhydrophobic top surface.

8. The apparatus of claim 1:
wherein said hydrophobic base has a plurality of through holes; and
wherein said first hydrophilic fluid flow structure is disposed on said top surface of said hydrophobic base over the through holes.

9. The apparatus of claim 1, further comprising:
a communications link coupled to the controller; and
a wireless computation device in communication with the controller through the communications link.

10. A digital droplet microflowmeter apparatus, comprising:
(a) a droplet nozzle with a superhydrophobic outer surface, one or more fluid channels and an orifice in the nozzle outer surface;
(b) a first electrode operably coupled to the droplet nozzle;
(c) a droplet receiver with a hydrophilic outer surface; and
(d) a second electrode operably coupled with the droplet receiver;
(e) wherein a transient fluid bridge is formed between the droplet nozzle and the droplet receiver from fluid emerging from the orifice of the droplet nozzle closing the circuit between the first and second electrodes.

11. The apparatus of claim 10, said droplet receiver further comprising a post with a hydrophilic surface oriented perpendicularly to a planar outer surface of the droplet receiver.

12. The apparatus of claim 10, said droplet receiver further comprising a plurality of drains oriented opposite of the orifice of the droplet nozzle.

13. The apparatus of claim 10, further comprising:
a controller configured to receive signals from the first and second electrodes; and
a display connected to the controller.

14. The apparatus of claim 10, further comprising:
a controller configured to receive signals from the first and second electrodes;
a communications link coupled to the controller;
a wireless computation device in communication with the controller through the communications link; and
a display connected to the wireless computation device.

15. The apparatus of claim 14, wherein said communications link comprises a Bluetooth communications link and said wireless computation device comprises a smart telephone.

16. The apparatus of claim 14, said wireless computation device further comprising:
(a) a processor; and
(b) a non-transitory memory storing instructions executable by the processor;
(c) wherein said instructions, when executed by the processor, perform steps comprising:
(i) receiving transmitted signals from a controller of detected changes in impedance between electrodes upon formation of the transient fluid bridge between the droplet nozzle and the droplet receiver;
(ii) calculating a rate of droplet flow;
(iii) calculating flow volume; and
(iv) displaying the volume and rate of droplet flow on the display.

17. The apparatus of claim 16, wherein said instructions when executed by the processor further perform steps comprising recording calculated flow rates and flow volumes over time.

18. A method for measuring ultralow fluid flow rates, the method comprising:
(a) partially expressing a droplet of fluid from an orifice of a nozzle;
(b) forming a transient fluid bridge between the partially expressed droplet and a droplet receiver;
(c) detecting changes in impedance with a detector;
(d) fully transferring the droplet from the orifice of the nozzle to the receiver; and
(e) removing the droplet from the receiver.

19. The method of claim 18, further comprising:
producing a signal from the detector;
transmitting produced signals from the detector to a wireless computation device;
calculating a rate of droplet flow;
calculating droplet flow volume; and
displaying the calculated flow rate and flow volume on a display.

20. The method of claim 19, further comprising recording calculated flow rates and flow volumes over time.

* * * * *